(12) United States Patent
Kurihara

(10) Patent No.: US 10,307,304 B2
(45) Date of Patent: Jun. 4, 2019

(54) ABSORBENT ARTICLE

(71) Applicant: DAIO PAPER CORPORATION, Ehime (JP)

(72) Inventor: Ryoko Kurihara, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 235 days.

(21) Appl. No.: 15/316,277

(22) PCT Filed: Jun. 11, 2015

(86) PCT No.: PCT/JP2015/066843
§ 371 (c)(1),
(2) Date: Dec. 5, 2016

(87) PCT Pub. No.: WO2015/190546
PCT Pub. Date: Dec. 17, 2015

(65) Prior Publication Data
US 2017/0143559 A1    May 25, 2017

(30) Foreign Application Priority Data

Jun. 13, 2014  (JP) ................. 2014-122036

(51) Int. Cl.
*A61F 13/15*     (2006.01)
*A61F 13/47*     (2006.01)
(Continued)

(52) U.S. Cl.
CPC .......... *A61F 13/4704* (2013.01); *A61F 13/15* (2013.01); *A61F 13/511* (2013.01); *A61F 13/51104* (2013.01); *A61F 13/539* (2013.01)

(58) Field of Classification Search
CPC .......... A61F 13/51108; A61F 13/15707; A61F 13/4756; A61F 13/536; A61F 13/58;
(Continued)

(56) References Cited

U.S. PATENT DOCUMENTS

| 2003/0078553 | A1 | 4/2003 | Wada et al. |
| 2006/0116652 | A1* | 6/2006 | Miura ............... A61F 13/15203 604/380 |

(Continued)

FOREIGN PATENT DOCUMENTS

| EP | 2277482 | 1/2011 |
| EP | 2281536 | 2/2011 |

(Continued)

OTHER PUBLICATIONS

International Search Report dated Sep. 1, 2015.
(Continued)

*Primary Examiner* — Jacqueline F Stephens
(74) *Attorney, Agent, or Firm* — IPUSA, PLLC

(57) ABSTRACT

An absorbent article (1) includes a permeable front-side sheet (3), a back-side sheet (2), an absorber (4) disposed between the permeable front-side sheet and the back-side sheet, and an embossment (10) formed in the front surface of the permeable front-side sheet (3). The embossment (10) includes bent parts (30) at which an embossment direction abruptly changes. An outer edge of each of the bent parts (30) is an angled part (31), and an inner edge of each of the bent parts (30) is a curved part (32).

6 Claims, 3 Drawing Sheets

(51) Int. Cl.
*A61F 13/511* (2006.01)
*A61F 13/539* (2006.01)

(58) Field of Classification Search
CPC .......... A61F 13/15764; A61F 13/15642; A61F 13/15406; A61F 13/49015; A61F 13/532; A61F 13/587
USPC ............................ 604/378, 379, 380, 385.01
See application file for complete search history.

(56) References Cited

U.S. PATENT DOCUMENTS

| | | | |
|---|---|---|---|
| 2006/0116653 A1 | 6/2006 | Munakata et al. | |
| 2006/0276767 A1* | 12/2006 | Ueminami | A61F 13/4702 604/385.31 |
| 2011/0130737 A1* | 6/2011 | Sagisaka | A61F 13/4704 604/380 |
| 2011/0251575 A1* | 10/2011 | Kuroda | A61F 13/4704 604/380 |
| 2011/0288514 A1 | 11/2011 | Kuroda et al. | |
| 2012/0095424 A1 | 4/2012 | Komatsu et al. | |

FOREIGN PATENT DOCUMENTS

| | | |
|---|---|---|
| EP | 2612636 | 7/2013 |
| JP | 3971150 | 9/2007 |
| JP | 2010-148706 | 7/2010 |
| JP | 2010-234031 | 10/2010 |
| JP | 4969437 | 7/2012 |
| JP | 2013-154016 | 8/2013 |
| JP | 2013-176509 | 9/2013 |
| JP | 2013-215388 | 10/2013 |

OTHER PUBLICATIONS

International Search Report for PCT/JP2015/050005 dated Mar. 17, 2015.
U.S. Office Action for U.S. Appl. No. 15/108,621 dated Apr. 6, 2018.
Notice of Allowance for U.S. Appl. No. 15/108,621 dated Oct. 22, 2018.

* cited by examiner

ABSORBENT ARTICLE

TECHNICAL FIELD

The present invention relates to absorbent articles such as a sanitary napkin, a pantyliner, and an incontinence pad for absorbing, for example, menstrual blood and a vaginal discharge. More particularly, the present invention relates to an absorbent article including embossments formed on its front side.

BACKGROUND ART

There exists an absorbent article such as a pantyliner, a sanitary napkin, or an incontinence pad that is made by sandwiching an absorber made of cellulose wadding such as ground pulp between an impermeable back-side sheet such as a polyethylene sheet or a polyethylene-sheet-laminated nonwoven fabric and a permeable front-side sheet such as a nonwoven fabric or a permeable plastic sheet.

As an improvement to such an absorbent article, a linear embossment is formed in the front surface of the permeable font-side sheet for various purposes. For example, Patent Document 1 discloses an absorbent article including side grooves that extend in the longitudinal direction of the absorbent article and are formed in side areas to the right and left in the width direction of an excretory facing area by compressing a front-side sheet and an absorber together. Each of the side grooves includes diagonal parts that join the ends of a straight part and extend inward or outward in boundary areas between the excretory facing area and front and rear areas.

Also, Patent Document 2 discloses an absorbent article including an embossment that includes a urination-opening facing embossment, and a front embossment and a rear embossment before and after the urination-opening facing embossment. The urination-opening facing embossment has a shape that swells outward in the width direction of the absorbent article. Also, at least a part of each of the front embossment and the rear embossment near the urination-opening facing embossment has a curved or linear shape that has a center of curvature outside of the absorbent article in the width direction and has a radius of curvature that is greater than or equal to the longitudinal dimension of the urination-opening facing embossment.

RELATED-ART DOCUMENTS

Patent Documents

Patent Document 1: Japanese Patent No. 4969437
Patent Document 2: Japanese Laid-Open Patent Publication No. 2013-176509

DISCLOSURE OF INVENTION

Problems to be Solved by the Invention

In the absorbent article of Patent Document 1, the joint between the straight part and the diagonal part of the side groove (embossment) forms a bent part at which the embossment direction abruptly changes. Because the outer edge and the inner edge of the bent part are angled, the direction of force applied to form the embossment abruptly changes. This causes problems such as wrinkles on a surface material and "floating" where the surface material is detached from an absorber.

In the absorbent article of Patent Document 2, the joint between the urination-opening facing embossment and each of the front embossment and the rear embossment forms a bent part at which the embossment direction abruptly changes. Because the outer edge and the inner edge of the bent part are curved, it is difficult to detect the bent part from the outside by the human eyes. For example, when the embossment is used as a scale to determine the amount of a body fluid absorbed by the absorber, the low detectability of the bent part makes it difficult to determine the amount of the absorbed body liquid.

In view of the above problems, one object of the present invention is to reduce the occurrence of wrinkles and floating at a bent part of an embossment when the embossment is formed, and to provide an absorbent article where the bent part is highly detectable.

Means for Solving the Problems

To solve the above problems, a first aspect of the invention provides an absorbent article that includes a permeable front-side sheet, a back-side sheet, an absorber disposed between the permeable front-side sheet and the back-side sheet, and an embossment formed in a front surface of the permeable front-side sheet. The embossment includes bent parts at which an embossment direction abruptly changes. An outer edge of each of the bent parts is an angled part, and an inner edge of each of the bent parts is a curved part.

According to the first aspect of the invention, the embossment formed in the front surface of the permeable front-side sheet includes bent parts at which the embossment direction abruptly changes. The outer edge of each of the bent parts is an angled part, and an inner edge of each of the bent parts is a curved part. The angled part makes it easier to visually detect the bent part. The curved part makes it possible to gradually change the direction of force applied to form the embossment, and thereby makes it possible to reduce the formation of wrinkles on a surface material and floating of the surface material.

A second aspect of the invention provides the absorbent article where at least one of the bent parts protrudes inward in a width direction of the absorbent article.

According to the second aspect of the invention, at least one of the bent parts protrudes inward in the width direction of the absorbent article. In this case, edges on the outside in terms of the bending direction and on the inside in terms of the width direction of the absorbent article are formed as the angled parts. With this configuration, when a pressure is applied by the leg from sides in the width direction of the absorbent article while the absorbent article is worn, the bent parts protruding inward easily enter the underside of the absorber, and the center portion of the absorber between the embossments rises toward the skin to better fit the skin.

A third aspect of the invention provides the absorbent article where the bent parts include a bent part protruding inward in a width direction of the absorbent article and a bent part protruding outward in the width direction that are sequentially arranged in a longitudinal direction of the absorbent article.

According to the third aspect of the invention, a bent part protruding inward in the width direction and a bent part protruding outward in the width direction are sequentially arranged in a longitudinal direction of the absorbent article. With this configuration, the embossments can better function as a scale to determine the amount of a body fluid absorbed by the absorber. Also, with the configuration where the bent parts bending in opposite directions are arranged sequentially, the flow of the body fluid along the embossments temporarily slows down at the bent parts. Thus, this configuration makes it possible to control the flow of the body fluid along the embossments so that the body fluid can be efficiently absorbed by the absorber.

A fourth aspect of the invention provides the absorbent article where the bent parts include at least three bent parts that are sequentially arranged in a longitudinal direction of the absorbent article such that a bent part protruding inward in a width direction of the absorbent article and a bent part protruding outward in the width direction are alternately arranged to form a zigzag shape.

According to the fourth aspect of the invention, at least three bent parts are sequentially arranged in the longitudinal direction of the absorbent article in a zigzag shape. With this configuration, the flow of the body fluid temporarily slows down at the bent parts. Thus, this configuration makes it possible to control the flow of the body fluid along the embossments.

A fifth aspect of the invention provides the absorbent article where the embossment is formed such that outer edges of all of the bent parts are angled parts and inner edges of all of the bent parts are curved parts.

According to the fifth aspect of the invention, the embossment is formed such that outer edges of all of the bent parts are angled parts and inner edges of all of the bent parts are curved parts. This configuration further improves the detectability of the embossment as well as the efficiency of forming the embossment.

A sixth aspect of the invention provides an absorbent article where high-compression parts are discretely arranged on a bottom of the embossment, and an area of each of the high-compression parts disposed in the bent parts is greater than an area of each of the high-compression parts disposed in other positions.

According to the sixth aspect of the invention, high-compression parts are discretely arranged on a bottom of the embossment, and an area of each of the high-compression parts disposed in the bent parts is greater than an area of each of the high-compression parts disposed in other positions. This configuration makes the bent parts more visually noticeable, and makes it easier to identify and use the embossment as a scale to determine the amount of the body fluid absorbed by the absorber.

A seventh aspect of the invention provides the absorbent article where high-compression parts are discretely arranged on a bottom of the embossment, and the high-compression parts are arranged discretely in an embossed groove such that at least one high-compression part is present on a line drawn in a longitudinal direction of the absorbent article.

According to the seventh aspect of the invention, the high-compression parts are preferably arranged discretely in the embossed groove such that at least one high-compression part is present on a line drawn in the longitudinal direction of the absorbent article. This configuration makes it possible to substantially evenly apply a pressure in an embossed groove during an embossing process, and thereby makes it possible to prevent formation of wrinkles during the embossing process due to the high-compression parts.

Advantageous Effect of the Invention

As discussed above, the present invention makes it possible to reduce the occurrence of wrinkles and floating at a bent part of an embossment when the embossment is formed, and to improve the detectability of the bent part.

DESCRIPTION OF EMBODIMENTS

<Basic Structure of Incontinence Pad 1>

Embodiments of the present invention are described below with reference to the accompanying drawings.

Figure 1:
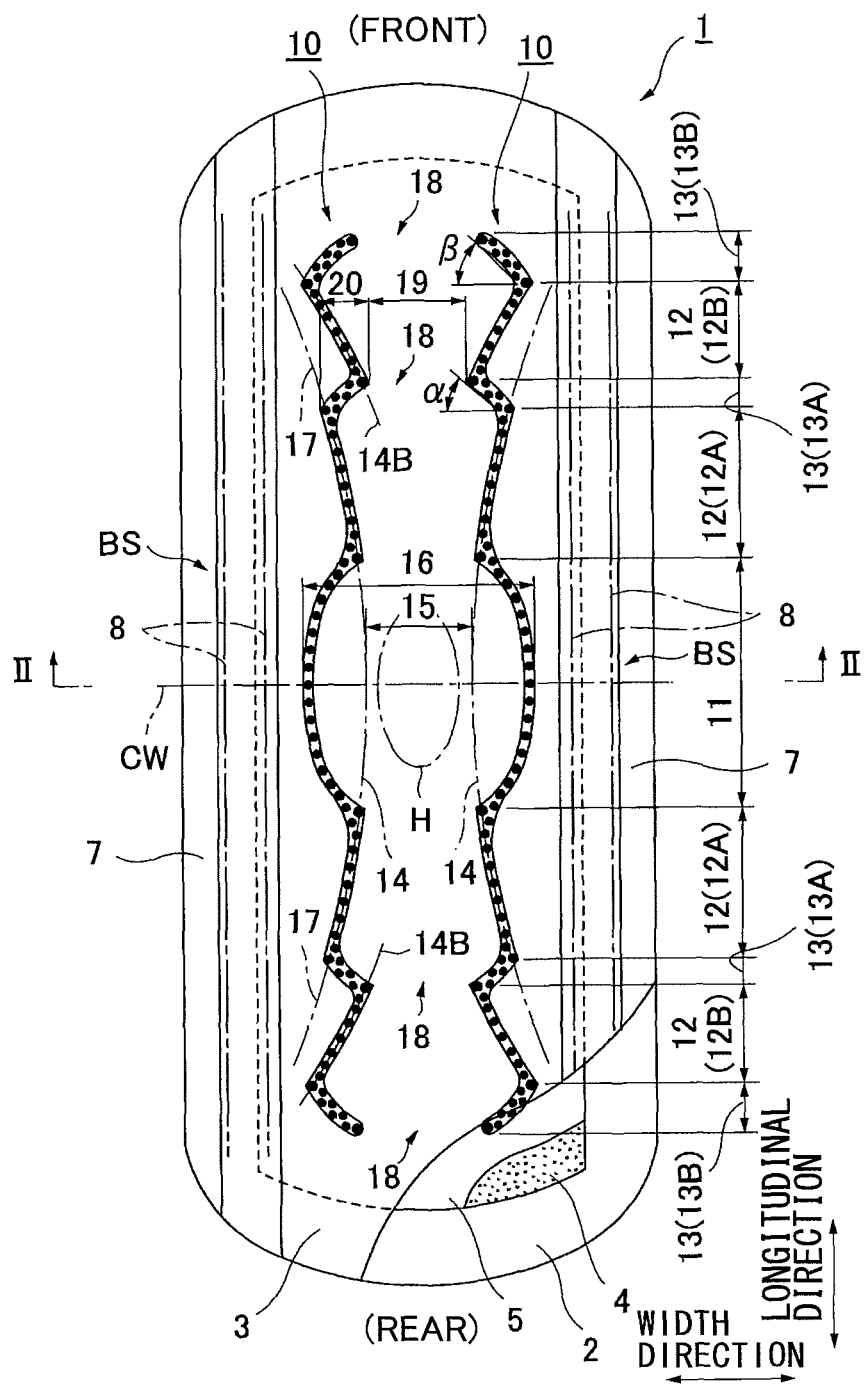
FIG. 1 is a partially cut-away view of an incontinence pad 1 according to the present invention.
Figure 2:
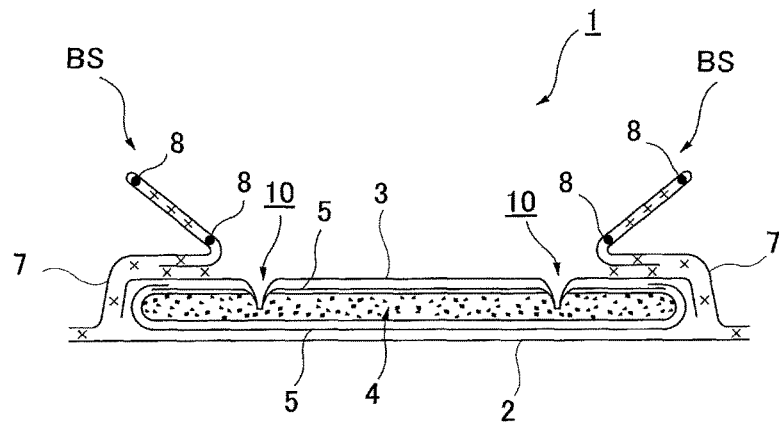
FIG. 2 is a cross-sectional view taken along line II-II of FIG. 1.

As illustrated by FIGS. 1 and 2, the incontinence pad 1 of the present invention includes an impermeable back-side sheet 2 such as a polyethylene sheet; a permeable front-side sheet 3 that allows, for example, urine to quickly pass through; an absorber 4 sandwiched between the sheets 3 and 4 and made of, for example, cotton-like pulp or synthetic pulp; an enveloping sheet 5 that is made of, for example, crepe paper or nonwoven fabric and envelops the absorber 4 to maintain the shape of the absorber 4 and to improve the diffusibility of the absorber 4; and side nonwoven fabrics 7 forming a pair of right and left solid gathers BS that rise from positions near the side edges of the absorber 4 toward the skin, and extend in the longitudinal direction across a predetermined area to cover at least a body-fluid ejection part H. At the end edges of the absorber 4 in the longitudinal direction, the outer edges of the impermeable back-side sheet 2 and the permeable front-side sheet 3 are bonded together with an adhesive such as a hot melt or by a bonding technique such as heat sealing. Also, at the side edges of the absorber 4, parts of the impermeable back-side sheet 2 extending laterally beyond the absorber 4 are bonded to the side nonwoven fabrics 7 with an adhesive such as a hot melt or by a bonding technique such as heat sealing. Also, as necessary, a hydrophilic second sheet (not shown) may be provided between the permeable front-side sheet 3 and the absorber 4.

The structure of the incontinence pad 1 is described in more detail below.

The impermeable back-side sheet 2 may be made of a sheet material such as polyethylene or polypropylene having at least a waterproof property. Also, a nonwoven fabric sheet that is made substantially impermeable by using a waterproof film (i.e., an impermeable back-side sheet including a waterproof film and a nonwoven fabric) may be used as the impermeable back-side sheet 2. In recent years, sheets having vapor permeability have been preferably used to prevent stuffiness. As a waterproof and vapor-permeable sheet, a microporous sheet is preferably used. A microporous sheet is obtained by melt-mixing an inorganic filler with an olefin resin such as polyethylene or polypropylene to form a sheet, and by stretching the sheet uniaxially or biaxially.

The permeable front-side sheet 3 is preferably made of a porous or nonporous nonwoven fabric or a porous plastic sheet. Examples of fiber materials of the nonwoven fabric include synthetic fibers made of olefin such as polyethylene or polypropylene, polyester, or polyamide; regenerated fibers such as rayon and cupra, and natural fibers such as cotton. The nonwoven fabric may be produced by any appropriate production method such as a spun lace method, a spun bond method, a thermal bond method, a melt blown method, or a needle punching method. Among these production methods, the spun lace method has an advantage in terms of flexibility and draping characteristics, and the thermal bond method has an advantage in terms of bulkiness and softness.

The absorber 4 may include, for example, absorbent fibers such as fluff pulp and a super absorbent polymer. In the example of FIG. 1, the absorber 4 has a substantially-oval shape in plan view that is long in the longitudinal direction of the incontinence pad 1. The super absorbent polymer is in the form of, for example, a granular powder, and is dispersed and mixed in pulp constituting the absorber 4.

The pulp may be made of cellulose fibers such as chemical pulp and dissolving pulp made from wood, or synthetic cellulose fibers such as rayon and acetate. In terms of the function and the price, softwood pulp with a long fiber length is more preferable than hardwood pulp. In the incontinence pad 1, the absorber 4 is enveloped by the enveloping sheet 5, and therefore the enveloping sheet 5 exists between the permeable front-side sheet 3 and the absorber 4. The highly-absorbent enveloping sheet 5 causes a body fluid such as urine to quickly diffuse and prevents the backflow of the body fluid. The mass per unit area of the pulp is between 100 g/m$^2$ and 800 g/m$^2$, and is preferably between 200 g/m$^2$ and 500 g/m$^2$.

Examples of the super absorbent polymer include crosslinked polyacrylate, self-crosslinked polyacrylate, a saponified product of crosslinked acrylate-vinyl acetate copolymer, crosslinked isobutylene-maleic anhydride copolymer, crosslinked polysulfonate, and partially-crosslinked water-swellable polymer such as polyethylene oxide or polyacrylamide. Among them, polymers including acrylic acid or acrylate are preferable in terms of the water absorption amount and the water absorption rate. The water absorbing power (absorption ratio) and the water absorption rate of the super absorbent polymer can be adjusted by adjusting the crosslink density and the crosslink density gradient during the production process. The mass per unit area of the super absorbent polymer is between 60 g/m$^2$ and 500 g/m$^2$, and is preferably between 100 g/m$^2$ and 450 g/m$^2$ in order to give a predetermined absorption capacity to the body-fluid ejection part and an area around the body-fluid ejection part.

Synthetic fibers may also be added to the absorber 4. The synthetic fibers may be made of, for example, polyolefin such as polyethylene or polypropylene, polyester such as polyethylene terephthalate or polybutylene terephthalate, polyamide such as nylon, or a copolymer of these polymers. Also, a mixture of two types of synthetic fibers may be used. Further, bicomponent fibers may be used. Examples of bicomponent fibers include a core-in-sheath fiber including a high-melting-point fiber as a core and a low-melting-point fiber as a sheath, a side-by-side fiber, and a split fiber. When using hydrophobic synthetic fibers, the synthetic fibers are preferably surface-treated with a hydrophilic agent so that the synthetic fibers have an affinity to the body fluid.

The absorber 4 may include a base portion and a medium-height portion where the amounts of pulp and polymer are greater than those in the base portion. Also, a polymer sheet may be provided in a portion of the absorber 4. When the absorber 4 includes the medium-height portion, embossments 10 described later are preferably formed outside of the medium-height portion.

The side nonwoven fabrics 7 are provided on the front side of the incontinence pad 1. The side nonwoven fabrics 7 extend in the longitudinal direction along the sides of the incontinence pad 1 and across the entire length of the incontinence pad 1. The peripheral parts of the side nonwoven fabrics 7 extend laterally, and the peripheral parts of the impermeable back-side sheet 2 also extend laterally. The peripheral parts of the side nonwoven fabrics 7 and the impermeable back-side sheet 2 are joined together with, for example, a hot-melt adhesive to form side flaps.

For the side nonwoven fabrics 7, a water-repellent nonwoven fabric or a hydrophilic nonwoven fabric may be used depending on the priorities of functions of the side nonwoven fabrics 7. For example, when priority is given to a function to prevent penetration of, e.g., urine or a function to improve the feel, a water-repellent nonwoven fabric such as SSMS, SMS, or SMMS coated with a silicon-, paraffin-, or alkyl chromic chloride-water repellent is preferably used. When priority is given to the absorbency of a body fluid, a hydrophilic nonwoven fabric is preferably used. For example, such a hydrophilic nonwoven fabric may be prepared by polymerizing a compound having a hydrophilic group such as an oxidation product of polyethylene glycol during the production process of synthetic fibers. Also, a hydrophilic nonwoven fabric may be prepared by processing synthetic fibers with metal salt such as stannic chloride to partially dissolve the surfaces of the synthetic fibers and give them porosity, and by depositing metal hydroxide on the synthetic fibers. The resulting synthetic fibers become swollen or porous and exhibit a hydrophilic property due to capillarity. The side nonwoven fabrics 7 may be produced using natural fibers, synthetic fibers, or regenerated fibers as a material according to any appropriate production method.

As illustrated in FIG. 2, an outer portion of the side nonwoven fabric 7 relative to its center in the width direction is bonded with an adhesive such as a hot melt to an area that extends from an inner position on the absorber 4, slightly beyond the side edge of the absorber 4, to the outer edge of the impermeable back-side sheet 2. On the other hand, an inner portion of the side nonwoven fabric 7 is folded back in the width direction. At least the end portion of the folded-back portion has a double-sheet structure. At least one, in this example, two elastic strings 8 are provided in the double-sheet structure. The elastic strings 8 are fixed at the ends or at any appropriate positions in the longitudinal direction. The ends of the folded-back portion in the napkin's longitudinal direction are bonded to a lower layer. As illustrated in FIG. 2, the middle portion of the folded-back portion in the napkin's longitudinal direction including the elastic strings 8 is raised due to the contraction of the elastic strings 8 and forms the solid gather BS on the front side.

<Embossment 10>

As illustrated in FIG. 1, a pair of embossments 10 are formed in the front surface of the permeable front-side sheet 3. The embossments 10 are apart from each other in the lateral direction. Each of the embossments 10 is formed by compressing parts of the permeable front-side sheet 3, the enveloping sheet 5, and the absorber 4 together from the front surface of the permeable front-side sheet 3.

As illustrated in FIG. 1, each embossment 10 includes a body-fluid ejection part embossment 11, longitudinal embossments 12, and diagonal embossments 13. In the example of FIG. 1, the longitudinal embossments include first longitudinal embossments 12A adjacent to the body-fluid ejection part embossment 11 (i.e., located at inner positions), and second longitudinal embossments 12B located farther from the center than the first longitudinal embossments 12A in the longitudinal direction. The diagonal embossments 13 include first diagonal embossments 13A that extend from the outer ends of the first longitudinal embossments 12A, and second diagonal embossments 13B that extend from the outer ends of the second longitudinal embossments 12B. In the example of FIG. 1, the embossment 10 is composed only of the body-fluid ejection part embossment 11, the longitudinal embossments 12, and the diagonal embossments 13. However, other embossments may be added as necessary.

A pair of body-fluid ejection part embossments 11 are formed in regions that include areas adjacent in the pad's width direction to the area corresponding to the body-fluid ejection part H. The body-fluid ejection part embossments 11 are embossed lines that extend along the longitudinal direction of the incontinence pad 1 and curve outward in the width direction of the incontinence pad 1. The body-fluid ejection part embossments 11 are apart from each other in the lateral direction. The body-fluid ejection part embossments 11 prevent laterally-outward diffusion of the body fluid that is absorbed by the absorber 4 between the right and left body-fluid ejection part embossments 11, and thereby prevent side leakage of the body fluid. Also, the body-fluid ejection part embossments 11 cause the body fluid, which flows laterally outward from the center of the front surface, to flow into grooves and thereby prevent the body fluid from flowing out in the width direction. The right and left body-fluid ejection part embossments are apart from each other in the pad's width direction and are independent from each other. The body-fluid ejection part embossment 11 has a shape that curves outward in the width direction. That is, the longitudinal center portion of the body-fluid ejection part embossment 11 is located farther from the center in the width direction than the longitudinal ends of the body-fluid ejection part embossment 11. For example, the body-fluid ejection part embossment 11 may be shaped like an arc or an ellipse. The body-fluid ejection part embossment 11 is preferably symmetric with reference to the center in the longitudinal direction of the body-fluid ejection part embossment 11 so that the body fluid is diffused evenly in the longitudinal direction.

In the present application, "an embossment is formed along the longitudinal direction of the incontinence pad 1" indicates that a straight line connecting the ends of the embossment extends substantially along the longitudinal direction of the incontinence pad 1. This includes a case where the straight line is parallel to the longitudinal direction line and a case where the angle between the straight line and the longitudinal direction line is within about ±40 degrees. Also, an embossed line is not necessarily a straight line. For example, an embossed line may be a curved line, a bent line, or a wavy line.

The longitudinal embossments 12 are pairs of embossed lines formed before and after the body-fluid ejection part embossments 11 along the longitudinal direction of the incontinence pad 1. The longitudinal embossments 12 in each pair are apart from each other in the lateral direction. The longitudinal embossments 12 prevent the body fluid in the absorber from diffusing in the pad's width direction and thereby prevent side leakage of the body fluid. Also, the longitudinal embossments 12 guide the body fluid to diffuse in the pad's longitudinal direction. Two or more pairs of the longitudinal embossments 12 are preferably formed before and after the body-fluid ejection part embossments 11 so that the diagonal embossments 13 described later can function as a scale. In the example of FIG. 1, two pairs of the longitudinal embossments 12 are formed before and after the body-fluid ejection part embossments 11. That is, the first longitudinal embossments 12A and the second longitudinal embossments 12B are arranged in this order from each side of the body-fluid ejection part embossments 11 (i.e., from the inside).

Each longitudinal embossment 12 is preferably shaped like a straight line or a curved line with respect to the pad's longitudinal direction. Although the longitudinal embossment 12 may be shaped like a straight line or a curved line that curves outward in the pad's width direction, the longitudinal embossment 12 is preferably shaped like a curved line that curves inward in the pad's width direction as in FIG. 1 so that the body fluid can smoothly diffuse in the absorber.

The first longitudinal embossments 12A are pairs of embossed lines disposed before and after the body-fluid ejection part embossments 11. The first longitudinal embossments 12A are connected to the longitudinal ends of the body-fluid ejection part embossments 11 and continuously extend from the longitudinal ends of the body-fluid ejection part embossments 11 in the pad's longitudinal direction. The first longitudinal embossments 12A in each pair are apart from each other in the lateral direction.

The second longitudinal embossments 12B are pairs of embossed lines that are located farther from the center than the first longitudinal embossments 12A in the longitudinal direction. The second longitudinal embossments 12B are formed substantially along the longitudinal direction of the incontinence pad 1 from positions that are different from the longitudinal outer ends of the first longitudinal embossments 12A. The second longitudinal embossments 12B in each pair are apart from each other in the lateral direction. The second longitudinal embossments 12B guide the body fluid diffused outside of the first longitudinal embossments 12A in the longitudinal direction. Forming the second longitudinal embossments 12B from positions different from the longitudinal outer ends of the first longitudinal embossments 12A makes it possible to prevent the body fluid flowing along the embossed lines of the first longitudinal embossments 12A from continuously flowing into the second longitudinal embossments 12B, and thereby makes it possible to suppress the diffusion of the body fluid flowing in the embossed grooves.

As illustrated in FIG. 1, the diagonal embossments 13 are pairs of embossed lines that extend from the outer ends of the longitudinal embossments 12 and are inclined toward the center in the width direction of the incontinence pad 1. The diagonal embossments 13 cause the body fluid diffusing outward along the longitudinal embossments 12 to flow toward the center in the width direction of the incontinence pad 1. Also, the diagonal embossments 13 can be used as a scale to measure the amount of the body fluid absorbed by the absorber 4. In the example of FIG. 1, the diagonal embossments 13 include the first diagonal embossments 13A that extend from the outer ends of the first longitudinal embossments 12A and are connected to the inner ends of the second longitudinal embossments 12B, and the second diagonal embossments 13B that extend from the outer ends of the second longitudinal embossments 12B.

Each diagonal embossment 13 is preferably shaped like a straight line or a curved line. As illustrated in FIG. 1, the diagonal embossment 13 is particularly preferably shaped like a circular arc that curves outward in the pad's longitudinal direction to smoothly guide the body fluid diffusing along the longitudinal embossment 12 to the inside of the incontinence pad 1.

The inner ends of the right and left diagonal embossments 13 are apart from each other in the width direction and a gap 18, where no embossment is present, is formed at the center in the pad's width direction. In other words, the diagonal embossments 13 extend from the outer ends of the longitudinal embossments 12, which are apart from each other in the lateral direction, toward the center in the pad's width direction up to the intermediate positions in the pad's width direction. The gap 18 makes it possible to prevent the embossments 10 from inhibiting the diffusion of the body fluid in the longitudinal direction in the absorber.

As described above, the first diagonal embossments 13A connect the outer ends in the pad's longitudinal direction of the first longitudinal embossments 12A with the inner ends in the pad's longitudinal direction of the second longitudinal embossments 12B. The inner ends of the second longitudinal embossments 12B are located closer to the center in the pad's width direction than the outer ends of the first longitudinal embossments 12A.

Also, the second diagonal embossments 13B extend from the outer ends in the pad's longitudinal direction of the second longitudinal embossments 12B toward the center in the pad's width direction up to the intermediate positions that are short of the pad's longitudinal center line.

In the incontinence pad 1 described above, the embossments 10 include the body-fluid ejection part embossments 11, the longitudinal embossments 12 that are formed along the pad's longitudinal direction before and after the body-fluid ejection part embossments 11, and the diagonal embossments 13 that extend from the outer ends of the longitudinal embossments 12 and are inclined toward the center in the pad's width direction. This configuration makes it possible to determine the degree of diffusion of the body fluid in the absorber by just visually examining the surface of the used incontinence pad 1 using the diagonal embossments 13 as a scale, and to select an appropriate pad size based on the determined degree of diffusion of the body fluid.

Also in the incontinence pad 1, the gaps 18 are formed between the ends of the right and left diagonal embossments 13 that are apart from each other in the width direction. This configuration prevents the embossments 10 from inhibiting the diffusion of the body fluid in the longitudinal direction in the absorber, and makes it possible to accurately determine the state of diffusion of the body fluid in the absorber. Also, because the diffusion of the body fluid is not inhibited, the body fluid does not stay near the body-fluid ejection part, and uncomfortable stickiness can be reduced.

As described above, the embossments 10 of the incontinence pad 1 are a pair of right and left embossed grooves that continuously extend in the pad's longitudinal direction, and include the body-fluid ejection part embossments 11, the longitudinal embossments 12, and the diagonal embossments 13. Each of the joints between the embossments 11, 12, and 13 forms a bent part 30 at which the embossment direction abruptly changes. The bent part 30 is a position at which two embossments inclined in opposite directions with reference to the pad's longitudinal direction are joined together. At the bent part 30, the embossment direction abruptly changes from the direction of an embossed groove before the bent part 30 to the direction of another embossed groove after the bent part 30. Accordingly, at the bent part 30, the embossed line protrudes outward or inward in the pad's width direction.

Figure 3:
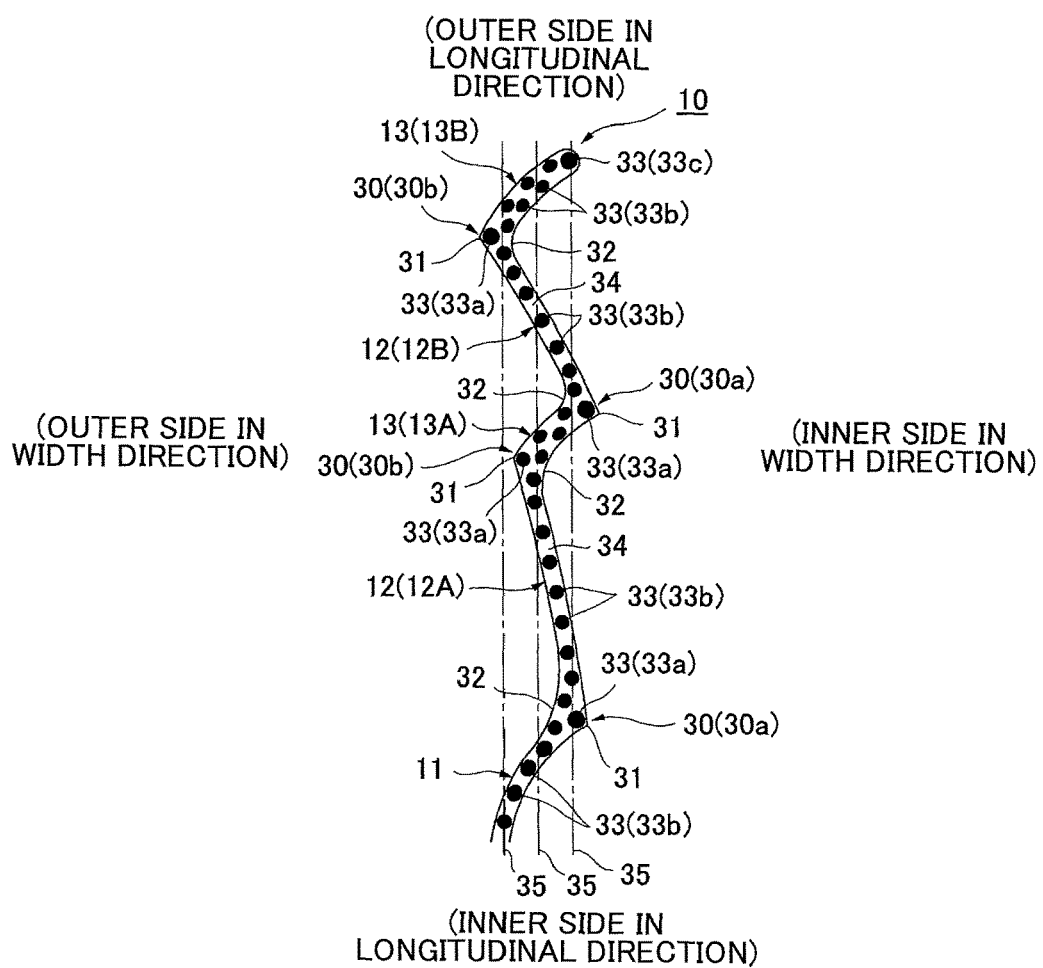
FIG. 3 is an enlarged plan view of an embossment 10.

The embossment 10 is formed such that the outer edge of the bent part 30 with respect to the bending direction is an angled part 31 and the inner edge of the bent part 30 with respect to the bending direction is a curved part 32. More specifically, as illustrated in FIG. 3, at a bent part 30a that protrudes inward in the pad's width direction, the angled part 31 is formed at an edge that is on the outside in terms of the bending direction and on the inside in terms of the pad's width direction, and the curved part 32 is formed at an edge that is on the inside in terms of the bending direction and on the outside in terms of the pad's width direction. On the other hand, at a bent part 30b that protrudes outward in the pad's width direction, the angled part 31 is formed at an edge that is on the outside in terms of the bending direction and also on the outside in terms of the pad's width direction, and the curved part 32 is formed at an edge that is on the inside in terms of the bending direction and also on the inside in terms of the pad's width direction.

Figure 4:
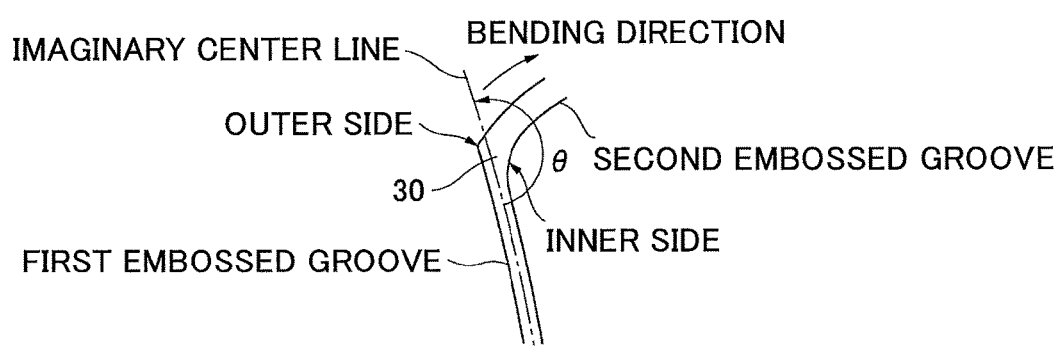
FIG. 4 is an enlarged view of a bent part 30.

As illustrated by FIG. 4, when first and second embossed grooves extending in different directions are joined at the bent part 30 and an imaginary line is drawn by extending the center line of the first embossed groove, the "outer edge" of the bent part 30 faces a direction opposite from the bending direction of the second embossed groove, and the "inner edge" faces the bending direction of the second embossed groove. That is, when θ indicates an angle around the bent part 30 on one side of the imaginary center line facing the bending direction of the second embossed groove, the "outer edge" exists on the other side of the imaginary center line corresponding to angles greater than θ, and the "inner edge" exists on the side of the imaginary center line corresponding to angles less than θ.

The angled part 31 is a part at which curved lines with different tangents intersect with each other, a part at which straight lines, which are not parallel, intersect each other, or a part at which a curved line and a straight line intersect with each other. However, because embossments are formed by compressing flexible materials such as an absorber and the ends of protruding embossments are chamfered in actual products, an angled part may not always have a perfect shape formed by intersecting straight lines. For this reason, in the present invention, the angled part 31 may indicate a part at which curved lines, straight lines, or a curved line and a straight line are connected to each other via a circular arc with a radius of curvature of less than or equal to 1 mm (R1 mm or less).

The curved part 32 is a part at which curved lines, straight lines, or a curved line and a straight line are connected to each other via a smooth circular arc, i.e., a rounded part. The radius of curvature of the circular arc constituting the curved part 32 is preferably between R2 and R22 mm.

Forming the inner and outer edges of the bent part 30 with the angled part 31 and the curved part 32 has advantageous effects as described below. The angled part 31 makes it easier to visually detect a bent part at which the direction of an embossment abruptly changes. The curved part 32 makes it possible to gradually and continuously change the direction of force applied to form an embossment. This in turn makes it possible to reduce the formation of wrinkles on a surface material (the permeable front-side sheet 3) and to prevent the occurrence of floating of the embossment where the surface material is detached from an absorber.

Also in the above embodiment, the angled part is formed at the inner edge of the bent part 30a protruding inward. When a pressure is applied in a direction from the outside toward the inside in the pad's width direction by an inside part of the groin while the incontinence pad 1 is worn, this configuration enables a part of the incontinence pad 1 between the right and left embossments 10 to easily rise toward the skin.

Also in the above embodiment, the outer edge of the bent part 30 is formed as the angled part 31 and the inner edge of the bent part 30 is formed as the curved part 32. Compared with a case where both of the outer and inner edges of the bent part 30 are formed as angled parts or curved parts, the above configuration makes it possible to form wider embossed grooves. This in turn makes it possible to more easily detect the bent part 30, and to more firmly emboss the bent part 30.

At least one of the bent parts 30 is preferably formed as the bent part 30a that protrudes inward in the width direction of the incontinent pad 1. In the example of FIG. 1, two bent parts 30a protruding inward in the width direction are formed before and after the body-fluid ejection part embossment 11. In this case, edges on the outside in terms of the bending direction and on the inside in terms of the pad's width direction are formed as the angled parts 31. With this configuration, when a pressure is applied by the leg in a direction from the outside toward the inside in the pad's width direction while the incontinence pad 1 is worn, the bent parts 30a protruding inward in the pad's width direction easily enter the underside of the absorber 4, and the center portion of the absorber 4 between the right and left embossments 10 rises toward the skin using the bent parts 30a as fulcrums to better fit the skin. Particularly, to make the center portion of the absorber 4 tightly fit the body-fluid ejection part H, the bent parts 30 at the joints between the body-fluid ejection part embossments 11 and the adjacent longitudinal embossments 12 (the first longitudinal embossments 12A) are preferably formed as the bent parts 30a that protrude inward in the pad's width direction.

Before and after the body-fluid ejection part embossments 11, the bent parts 30 are preferably formed such that the bent parts 30a protruding inward in the pad's width direction and the bent parts 30b protruding outward in the pad's width direction are sequentially arranged in the pad's longitudinal direction. With this configuration, the embossments 10 can better function as a scale to determine the amount of the body fluid absorbed by the absorber 4. Also, with the configuration where the bent parts 30a and 30b bending in opposite directions are arranged sequentially, the flow of the body fluid along the embossments 10 temporarily slows down at the bent parts 30. Thus, this configuration makes it possible to control the flow of the body fluid along the embossments 10 so that the body fluid can be efficiently absorbed by the absorber. Here, "sequentially arranging the bent parts 30a and 30b in the pad's longitudinal direction" indicates that the bent parts 30a and 30b are sequentially formed in the pad's longitudinal direction by the longitudinal embossments 12 and the diagonal embossments 13.

Before and after the body-fluid ejection part embossments 11, at least three bent parts 30, which are adjacent to each other in the pad's longitudinal direction, are preferably formed such that the bent parts 30a protruding inward in the pad's width direction and the bent parts 30b protruding outward in the pad's width direction are alternately arranged in a zigzag shape. With the configuration where the bent parts 30a and 30b are arranged in a zigzag shape, the flow of the body fluid along the embossments 10 temporarily slows down at the bent parts 30. This configuration makes it possible to control the flow of the body fluid along the embossments 10 so that the body fluid can be efficiently absorbed by the absorber 4.

As illustrated in FIG. 1, the embossments 10 are preferably formed such that the outer edges of all the bent parts 30 in terms of the bending direction become the angled parts 31 and the inner edges of all the bent parts 30 in terms of the bending direction become the curved parts 32. This configuration further improves the detectability of the embossments 10 as well as the efficiency of forming the embossments 10. In this case, the bent parts 30 before and after the body-fluid ejection part embossments 11 are preferably formed such that the bent parts 30a and the bent parts 30b are arranged alternately in a zigzag shape.

The groove bottom of the embossment 10 may be a flat surface compressed to a constant depth. However, as illustrated in FIG. 3, the bottom of the embossed groove is preferably patterned to include high-compression parts 33 (black areas) and low-compression parts 34 (white areas). Each high-compression part 33 is an area that is compressed to a greater depth than the surrounding areas. The high-compression part 33 has a shape that is composed of one or more of a circular shape, an oval shape, a semicircular shape, a rectangular shape, and a linear shape. In the example of FIG. 3, the high-compression part 33 has a circular shape. Forming the high-compression parts 33 makes it possible to reduce the flow of the body fluid along the embossed groove, to facilitate the penetration of the body fluid into the absorber, and to improve the shape retention of the embossed groove.

As illustrated in FIG. 3, among the high-compression parts 33, the area of respective high-compression parts 33a formed in the bent parts 30 is preferably greater than the area of respective high-compression parts 33b formed in other positions. In FIG. 3, a circular high-compression part 33a, which is slightly larger than other high-compression parts 33, is formed near the apex of the angled part 31 of each bent part 30. This configuration makes the bent parts 30 more visually noticeable, makes it easier to wear the incontinence pad 1 by using an area between the right and left body-fluid ejection part embossments 11 as a target, and makes it easier to identify and use the diagonal embossments 13 as a scale to determine the amount of the body fluid absorbed by the absorber 4. The area of the high-compression part 33a is preferably 1.2 to 2.5 times greater than the area of the high-compression part 33b.

As illustrated in FIG. 3, the area of respective high-compression parts 33c formed at the ends of the embossment 10 is also preferably greater than the area of the respective high-compression parts 33b formed in other positions. This configuration makes it possible to firmly join the surface material and the absorber 4 at the ends of the embossment, and makes it possible to prevent the surface material from being detached from the absorber 4 at the ends of the embossment.

As illustrated in FIG. 3, the high-compression parts 33 are preferably arranged discretely in the embossed groove such that at least one high-compression part 33 is present on a line drawn in the pad's longitudinal direction. That is, the high-compression parts 33 are arranged discretely in the continuous embossed groove such that each of imaginary longitudinal direction lines 35 drawn in the pad's longitudinal direction passes through at least one high-compression part 33. More specifically, in the longitudinal embossment 12 whose width is narrower than the diagonal embossment 13 and whose inclination angle with respect to the longitudinal direction lines 35 is smaller than that of the diagonal embossment 13, the high-compression parts 33 are arranged at intervals along the embossment direction in a single row. On the other hand, in the diagonal embossment 13 whose width is wider than the longitudinal embossment 12 and whose inclination angle with respect to the longitudinal direction lines 35 is larger than that of the longitudinal embossment 12, the high-compression parts 33 are arranged along the embossment direction in two staggered rows. When the line conveyance direction of the incontinence pad is the pad's longitudinal direction and an embossing process is performed using an embossing roll, this configuration makes it possible to substantially evenly apply a pressure in an embossed groove, and thereby makes it possible to prevent formation of wrinkles during the embossing process.

Next, the structure of the embossment 10 is described in more detail. As illustrated in FIG. 1, the first longitudinal embossments 12A before and after the body-fluid ejection part embossment 11 are preferably formed such that extension lines of the first longitudinal embossments 12A form a single circular arc 14 that curves inward in the width direction of the incontinence pad 1. Forming the first longitudinal embossments 12A along the circular arc 14 makes the body-fluid ejection part embossments 11 more noticeable than the first longitudinal embossments 12A. This in turn makes it possible to easily wear the incontinence pad 1 on a correct position on the body by bringing the portion between the body-fluid ejection part embossments 11 into contact with the body-fluid ejection part H. In the example of FIG. 1, the center of curvature of the circular arc 14 is positioned on a lateral center line CW of the incontinence pad 1 so that the first longitudinal embossments 12A are arranged symmetrically with respect to the lateral center line CW.

As illustrated in FIG. 1, the first longitudinal embossments 12A are preferably arranged such that a narrowest position 15, at which the distance between the right and left circular arcs 14 is smallest, matches or becomes close to a widest position 16 at which the distance between the right and left body-fluid ejection part embossments 11 protruding outward in the width direction is largest. In the example of FIG. 1, the narrowest position 15 of the circular arcs 14 and the widest position 16 of the body-fluid ejection part embossments 11 are both on the same lateral center line CW of the incontinence pad 1. This configuration makes it possible to wear the incontinence pad 1 on a correct position by aligning the center of the body-fluid ejection part embossments 11 with the body-fluid ejection part H. Here, "the narrowest position 15 is close to the widest position 16" indicates that the distance between the narrowest position 15 and the widest position 16 is sufficiently small compared with the length of the body-fluid ejection part embossments 11 in the pad's longitudinal direction, i.e., one fifth or less of the length of the body-fluid ejection part embossments 11 in the pad's longitudinal direction.

As illustrated in FIG. 1, similarly to the first longitudinal embossments 12A, the second longitudinal embossments 12B are preferably formed along a single circular arc 14B that curves inward in the pad's width direction.

As illustrated in FIG. 1, the second longitudinal embossments 12B are preferably formed so as not to coincide with extension lines 17 formed by extending the first longitudinal embossments 12A outward. This configuration makes it difficult for the body fluid flowing along the first longitudinal embossments 12A to flow into the second longitudinal embossments 12B, and thereby makes it possible to suppress the diffusion of the body fluid along embossed grooves. Here, when the extension line 17 is drawn to pass through the center in the width direction of the first longitudinal embossment 12A, the extension line 17 preferably does not pass through the width of the second longitudinal embossment 12B. More preferably, the distance between the side edge of the second longitudinal embossment 12B and the extension line 17 is greater than the width of the second longitudinal embossment 12B. The extension line has the same shape as the first longitudinal embossment 12A. For example, when the first longitudinal embossment 12A is formed along the circular arc 14 as in FIG. 1, the extension line 17 is a circular arc obtained by extending the circular arc 14 outward.

As illustrated in FIG. 1, the second longitudinal embossments 12B are preferably formed at positions that are closer to the center in the pad's width direction than the extension lines 17 of the first longitudinal embossments 12A. This configuration makes it possible to suppress the diffusion of the body fluid in the pad's width direction, and thereby makes it possible to reliably prevent the side leakage of the body fluid.

As illustrated in FIG. 1, an angle α between the first diagonal embossment 13A and the width direction line of the incontinent pad 1 is less than or equal to 45 degrees, and is preferably between 20 and 45 degrees. This configuration makes it possible to reliably cause the body fluid flowing along the first longitudinal embossment 12A to flow toward the center and to be absorbed by the absorber. This configuration also makes it possible to cause the body fluid diffusing in the absorber to diffuse toward the center. When the first diagonal embossment 13A has a curved shape, the angle α may be represented by an angle between the width direction line and a line connecting the joint between the first diagonal embossment 13A and the first longitudinal embossment 12A and the joint between the first diagonal embossment 13A and the second longitudinal embossment 12B.

Also, as illustrated in FIG. 1, an angle β between the second diagonal embossment 13B and the width direction line of the incontinent pad 1 is less than or equal to 60 degrees, and is preferably greater than or equal to the angle α and less than or equal to 60 degrees. This configuration makes it possible to surround a large area with the second longitudinal embossments 12B and the second diagonal embossments 13B so that the body fluid flowing outward beyond the first longitudinal embossments 12A can be more reliably absorbed by the absorber.

As illustrated in FIG. 1, a gap width 19 of the gap 18 between the right and left diagonal embossments 13 is one to three times greater than a diagonal width 20 representing a width in the pad's width direction of the diagonal embossments 13, and is preferably 1.5 to 2.5 times greater than the diagonal width 20. Making the gap width 19 greater than the diagonal width 20 makes it possible to secure a diffusion path with a sufficient width for the body fluid diffusing in the absorber in the pad's longitudinal direction. This in turn prevents the inhibition of natural diffusion of the body fluid in the longitudinal direction of the absorber, prevents the body fluid from staying between the body-fluid ejection part embossments 11, and reduces stickiness.

The embossment 10 is preferably symmetrical in the longitudinal direction with respect to the center of the body-fluid ejection part embossment 11 or with respect to the lateral center line CW in the case of the incontinence pad 1 of FIG. 1. Particularly, arranging the diagonal embossments 13 symmetrically in the longitudinal direction makes it possible to accurately determine the amount of absorbed body fluid based on the diffusion of the body fluid after the incontinence pad 1 is used.

The longitudinal embossment 12 is preferably formed such that the outer side of the longitudinal embossment 12 in the pad's longitudinal direction is inclined outward in the pad's width direction with respect to the longitudinal direction line. This configuration makes it possible to not inhibit the natural diffusion where the body fluid diffuses outward in the pad's longitudinal direction from an area between the body-fluid ejection part embossments 11 and then diffuses outward in the pad's width direction, and allows the body fluid to smoothly diffuse in the absorber 4.

As described above, the outer side of the longitudinal embossment 12 in the pad's longitudinal direction is inclined outward in the pad's width direction with respect to the longitudinal direction line of the incontinence pad 1. The inclination angle of the second longitudinal embossment 12B located farther from the center than the first longitudinal embossment 12A is preferably greater than the inclination angle of the first longitudinal embossment 12A. More specifically, when γ indicates an inclination angle between the first longitudinal embossment 12A and the longitudinal direction line and 5 indicates an inclination angle between the second longitudinal embossment 12B and the longitudinal direction line, γ<δ is satisfied. The inclination angle δ is preferably greater than the inclination angle γ by about 15 to 20 degrees. The inclination angle γ of the first longitudinal embossment 12A is less than or equal to 20 degrees, preferably between 5 and 15 degrees, and more preferably between 8 and 12 degrees. The inclination angle δ of the second longitudinal embossment 12B is less than or equal to 37 degrees, preferably between 22 and 32 degrees, and more preferably between 25 and 29 degrees.

Even when continuous embossments are formed along the longitudinal direction as in the incontinence pad 1, increasing the inclination angle of the embossments toward the outer end in the pad's longitudinal direction makes it possible to suppress the diffusion of the body fluid in the pad's longitudinal direction along the embossments particularly at outer positions in the pad's longitudinal direction where the inclination angle is large. This in turn makes it easier to determine the state of diffusion of the body fluid absorbed by the absorber.

The groove widths of the body-fluid ejection part embossment 11, the longitudinal embossment 12, and the diagonal embossment 13 may be the same or different from each other. When the embossments are formed with different groove widths, the groove width of the diagonal embossment 13 is preferably made greater than the groove width of the longitudinal embossment 12. More specifically, as illustrated in FIG. 1, when S13 indicates the groove width of the diagonal embossment 13 and S12 indicates the groove width of the longitudinal embossment 12, S13>S12 is preferably satisfied. The groove width S13 of the diagonal embossment 13 is preferably 1.3 to 2 times greater than the groove width S12 of the longitudinal embossment 12. The groove width indicates the width of the groove bottom in cross-sectional view of an embossment. When the high-compression parts 33 are formed on an embossment bottom that is a low-compression part, the width of the low-compression part may be employed.

With the configuration where the groove width of the diagonal embossments 13 is greater than the groove width of the longitudinal embossments 12, the body fluid that has flowed along the longitudinal embossments 12 is temporarily accumulated at the diagonal embossments 13, and the diffusion of the body fluid along the embossed grooves is suppressed. This in turn makes it easier to observe the state of diffusion of the body fluid that has been absorbed by the absorber rather than the diffusion of the body fluid that has flowed along the embossments.

Other Embodiments

The above embodiment is described using an incontinence pad as an example. However, the present invention may also be applied to an absorbent article such as a sanitary napkin. In such a case, the materials and the sizes of components may be changed as necessary to suit the characteristics of an absorbent article. For example, when the present invention is applied to a sanitary napkin, the mass per unit area of the super absorbent polymer in the absorber 4 is between 5 g/m$^2$ and 200 g/m$^2$, and is preferably between 5 g/m$^2$ and 150 g/m$^2$.

EXPLANATION OF REFERENCE NUMERALS

1 incontinence pad, 2 impermeable back-side sheet, 3 permeable front-side sheet, 4 absorber, 5 enveloping sheet, 7 side nonwoven fabric, 8 elastic string, 10 embossment, 11 body-fluid ejection part embossment, 12 longitudinal embossment, 12A first longitudinal embossment, 12B second longitudinal embossment, 13 diagonal embossment, 13A first diagonal embossment, 13B second diagonal embossment, 14 circular arc, 15 narrowest position, 16 widest position, 18 gap, 30 bent part, 31 angled part, 32 curved part, 33 high-compression part, 34 low-compression part

The invention claimed is:

1. An absorbent article, comprising:
   a permeable front-side sheet;
   a back-side sheet;
   an absorber disposed between the permeable front-side sheet and the back-side sheet; and
   an embossment formed in a front surface of the permeable front-side sheet, wherein
   the embossment includes bent parts at which an embossment direction abruptly changes;
   each of the bent parts protrudes inward or outward in a width direction of the absorbent article;
   an outer edge, which faces in a direction of the protrusion, of each of the bent parts is an angled part; and
   an inner edge, which faces in a direction opposite the direction of the protrusion, of each of the bent parts is a curved part.

2. The absorbent article as claimed in claim 1, wherein the bent parts include a bent part protruding inward in the width direction of the absorbent article and a bent part protruding outward in the width direction that are sequentially arranged in a longitudinal direction of the absorbent article.

3. The absorbent article as claimed in claim 1, wherein the bent parts include at least three bent parts that are sequentially arranged in a longitudinal direction of the absorbent article such that a bent part protruding inward in the width direction of the absorbent article and a bent part protruding outward in the width direction are alternately arranged to form a zigzag shape.

4. The absorbent article as claimed in claim 1, wherein the embossment is formed such that outer edges of all of the bent parts are angled parts and inner edges of all of the bent parts are curved parts.

5. The absorbent article as claimed in claim 1, wherein
   high-compression parts are discretely arranged on a bottom of the embossment; and
   an area of each of the high-compression parts disposed in the bent parts is greater than an area of each of the high-compression parts disposed in other positions.

6. The absorbent article as claimed in claim 1, wherein
   high-compression parts are discretely arranged on a bottom of the embossment; and
   the high-compression parts are arranged discretely in an embossed groove such that at least one high-compression part is present on a line drawn in a longitudinal direction of the absorbent article.

* * * * *